(12) United States Patent
Porter et al.

(10) Patent No.: US 7,604,617 B2
(45) Date of Patent: Oct. 20, 2009

(54) PERCUTANEOUSLY IMPLANTABLE MEDICAL DEVICE CONFIGURED TO PROMOTE TISSUE INGROWTH

(75) Inventors: Christopher H. Porter, Woodinville, WA (US); Claude A. Vidal, Santa Barbara, CA (US); Russ J. Redmond, Goleta, CA (US); Byron L. Moran, Santa Barbara, CA (US)

(73) Assignee: Medical Research Products-B, Inc., Santa Clarita, CA (US)

( * ) Notice: Subject to any disclaimer, the term of this patent is extended or adjusted under 35 U.S.C. 154(b) by 357 days.

(21) Appl. No.: 10/821,383

(22) Filed: Apr. 9, 2004

(65) Prior Publication Data

US 2004/0204686 A1    Oct. 14, 2004

Related U.S. Application Data

(60) Provisional application No. 60/462,265, filed on Apr. 12, 2003.

(51) Int. Cl.
*A61M 5/32* (2006.01)
(52) U.S. Cl. .................................. 604/175; 623/10
(58) Field of Classification Search ............ 604/175; 606/132; 623/10
See application file for complete search history.

(56) References Cited

U.S. PATENT DOCUMENTS

| | | | | |
|---|---|---|---|---|
| 4,648,391 A | * | 3/1987 | Ellis | 128/846 |
| 4,668,222 A | * | 5/1987 | Poirier | 604/175 |
| 5,360,448 A | * | 11/1994 | Thramann | 606/60 |
| 5,814,104 A | * | 9/1998 | Beoni | 623/10 |
| 5,895,426 A | * | 4/1999 | Scarborough et al. | 623/17.16 |
| 5,931,838 A | * | 8/1999 | Vito | 606/61 |
| 6,955,677 B2 | * | 10/2005 | Dahners | 606/69 |

FOREIGN PATENT DOCUMENTS

| | | | |
|---|---|---|---|
| EP | 0367354 | * | 5/1990 |
| EP | 367354 A1 | * | 5/1990 |
| EP | 0 367 354 B1 | | 2/1993 |

OTHER PUBLICATIONS

J. A. Jansen et al., Tissue reaction to soft-tissue anchored percutaneous implants in rabbits, Journal of Biomedical Material Research, vol. 28, 1047-1054 (1994), John Wiley &.

* cited by examiner

*Primary Examiner*—Nicholas D Lucchesi
*Assistant Examiner*—Christopher D Koharski
(74) *Attorney, Agent, or Firm*—Freilich, Hornbaker & Rosen (57) ABSTRACT

An implantable device including a housing having a stud projecting percutaneously through an incision in the patient's skin. The stud defines a peripheral surface extending longitudinally inwardly from the stud outer end. The longitudinal peripheral surface is used as a substrate to carry a peripheral fibrous layer which extends longitudinally along the stud from its outer end adjacent to the skin incision to below the patient's epidermal and dermal skin layers for promoting laterally directed soft tissue ingrowth. The housing also defines a lateral shoulder surface oriented substantially perpendicular to the longitudinal peripheral surface. The shoulder surface also carries a porous layer conducive to promoting tissue ingrowth. The porous layers on the device allows tissue ingrowth into the interstices of both porous layers to form an enhanced infection resistant barrier while also providing improved device anchoring.

15 Claims, 10 Drawing Sheets

PERCUTANEOUSLY IMPLANTABLE MEDICAL DEVICE CONFIGURED TO PROMOTE TISSUE INGROWTH

RELATED APPLICATIONS

This application claims the benefit of U.S. provisional application 60/462,265 filed Apr. 12, 2003.

FIELD OF THE INVENTION

This invention relates generally to medical devices intended to be surgically implanted in a patient's body. More particularly, the invention is directed to an implantable percutaneous device, and method of implantation, especially configured to promote soft tissue ingrowth for creating an infection resistant barrier and for anchoring the implanted device in place.

BACKGROUND OF THE INVENTION

It is generally known that a porous outer surface can be used on an implantable medical device to promote bone ingrowth to facilitate device anchoring. It has also been suggested that the application of a porous surface to a percutaneous implantable device can be helpful for promoting tissue ingrowth. For example, see European Patent Publication 0367354B1 published Sep. 5, 1990 entitled "A percutaneous implant". It is also noted that so called "dacron cuffs" have been used to accommodate tissue ingrowth for anchoring percutaneous catheters.

SUMMARY OF THE INVENTION

The present invention is directed generally to medical devices and more particularly to a structural configuration and method of implantation for promoting tissue ingrowth around a percutaneously projecting portion, or stud, of the medical device so as to create an infection resistant barrier, provide effective anchoring and inhibit marsupialization (which reduces vascularization of the local tissue).

An implantable device in accordance with the invention includes a housing having a projecting stud defining an outer end and a peripheral surface extending longitudinally inwardly from said outer end. A longitudinally extending porous peripheral layer is formed on the peripheral surface characterized by a porosity conducive to promoting tissue ingrowth. When the device is implanted, the stud projects through a skin incision and places the porous peripheral layer adjacent to the skin surrounding the incision. The device is intended to be implanted so that the porous layer is oriented substantially perpendicular to the patent's skin plane adjacent to the incision site and extends longitudinally below the skin surface.

A porous layer in accordance with the invention is preferably formed by mounting a layer of fibrous material on the projecting stud of the implantable device housing. The fibrous layer is preferably fabricated from bio compatible metallic materials, such as titanium, nitinol, silver, or stainless steel, or from polymeric materials, such as polyolefins, Teflon, nylon, Dacron, or silicone. Fibers can be wound directly onto the housing stud or alternatively a separate structure (e.g., mesh or sintered polymeric or metallic material) can be fabricated and then attached to the stud using mechanical or adhesive techniques. To adequately promote soft tissue ingrowth, the resulting fibrous layer should preferably contain pore sizes on the order of 50 to 200 microns with a porosity of 60 to 95%.

A preferred implantable device in accordance with the invention includes a housing having a stud projecting percutaneously through an incision in the patient's skin. The stud defines a peripheral surface extending longitudinally inwardly from the stud outer end. The longitudinal peripheral surface is used as a substrate to carry the aforementioned fibrous layer. The peripheral fibrous layer is located so that when implanted, it extends to below the patient's epidermal and dermal skin layers for promoting laterally directed soft tissue ingrowth.

In accordance with the invention, the housing also defines a lateral shoulder surface oriented substantially perpendicular to the longitudinal peripheral surface. The shoulder surface, when implanted, is located just inwardly from the patient's outer skin surface. The shoulder surface also carries a porous layer conducive to promoting tissue ingrowth. The provision of both lateral and longitudinal porous layers on the device allows tissue ingrowth, i.e., tissue growth into the interstices of both porous layers, to promote vascularization and form an enhanced infection resistant barrier while also providing improved device anchoring.

Moreover, it may sometimes be desirable to selectively incorporate appropriate substances into, or adjacent to, the porous layers for various medical reasons such as promoting tissue healing and infection resistance and inflammation. Such substances are known in the literature and include, e.g., antibiotics, silver compounds, and steroid based agents.

Embodiments of the invention can be advantageously used with a wide variety of medical devices adapted for percutaneous implantation. By way of example, such devices include implantable hearing aids which can percutaneously project into the ear canal and catheters, cables, and/or sensors which can project percutaneously to provide access to various internal sites, e.g., access to the abdominal cavity, to the inner eye, to the circulatory system, etc.

DETAILED DESCRIPTION

Figure 1:
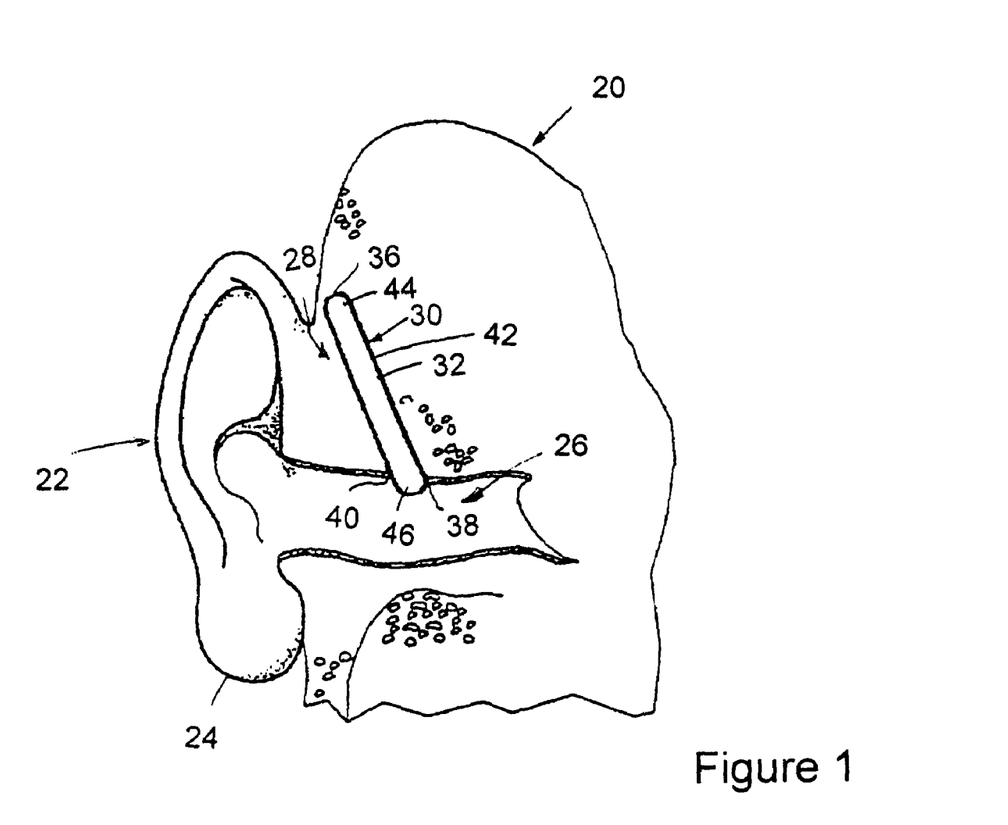
FIG. 1 schematically depicts an exemplary medical device (i.e., a hearing aid, percutaneously implanted in a patient's ear canal) which can advantageously utilize the teachings of the present invention.

Attention is initially directed to FIG. 1 which schematically depicts an exemplary application of the teachings of the invention. FIG. 1 represents a fragmentary front view of a patient's head 20 (i.e., as seen when looking at the patient's face) showing the patient's ear 22, pinna 24 (sometimes referred to as "auricle"), and an ear canal 26. The soft tissue space behind the pinna 24 is often referred to as the retro-auricular space or cavity 28.

FIG. 1 also depicts a generic hearing aid 30 implanted within a recess 32 behind the patient's ear canal 26. The recess 32 can be readily formed by a relatively simple surgical procedure involving for example, tunneling through the space 28. The recess nominally extends from a proximal end 36 to a distal end 38 located at an incision site 40 opening into the ear canal 26. The hearing aid 30 depicted in FIG. 1 is comprised of a generally elongate, e.g., cylindrical, tubular housing 42 having a proximal end 44 and a distal end 46. The housing 42 is preferably formed of a biocompatible material, e.g., titanium.

The tubular housing 42 typically contains electronic circuitry for driving a sound generator, i.e., an electroacoustic transducer (not shown) located within the housing proximate to the distal end 46. The housing distal end, as shown in FIG. 1, preferably projects percutaneously through the incision site 40 into the ear canal 26 to locate the transducer in or immediately adjacent to the ear canal.

Figure 2:
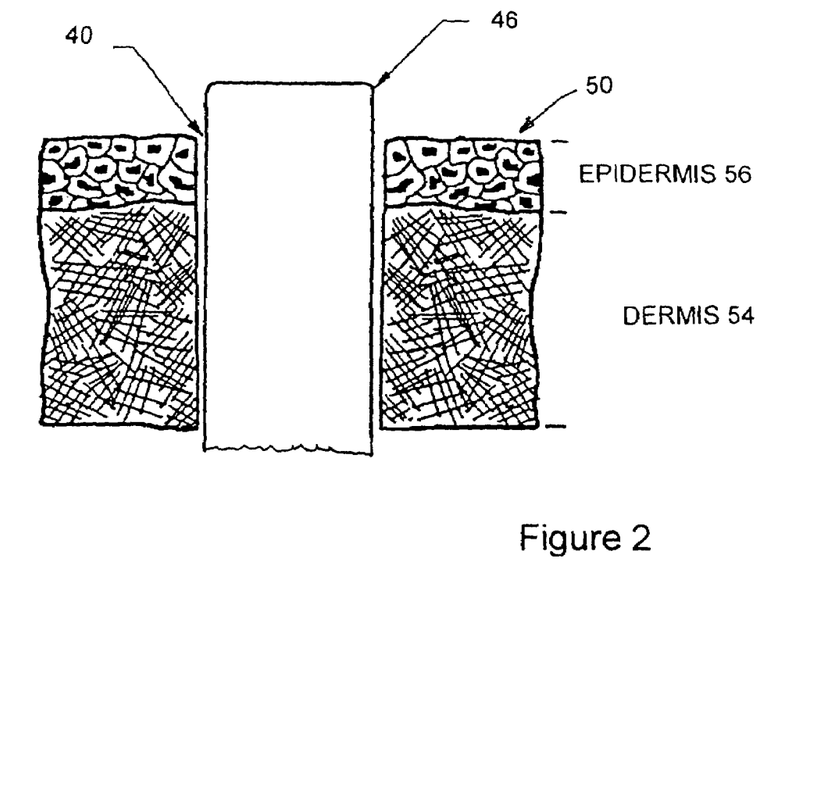
FIG. 2 is an enlarged schematic representation showing a conventional medical device penetrating the epidermis and dermis skin layers shortly after implantation.
Figure 3:
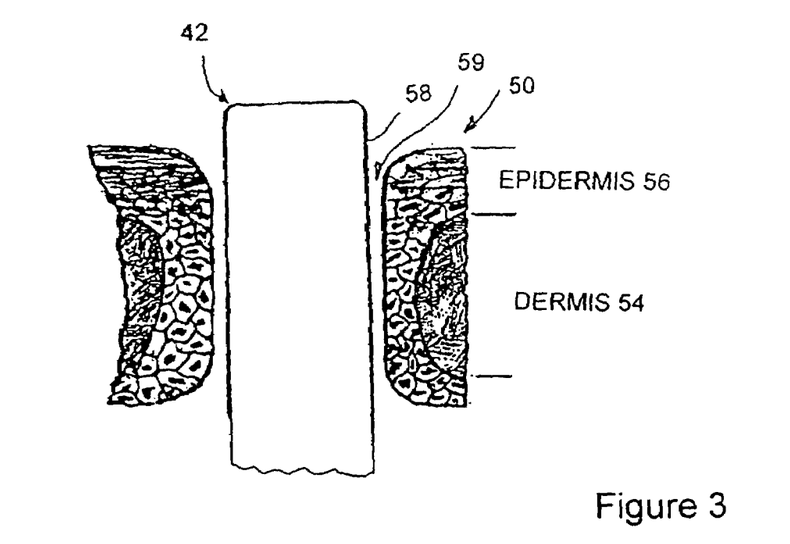
FIG. 3 is a schematic representation similar to FIG. 2 showing skin downgrowth around the conventional medical device typically occurring after implantation.

FIG. 2 schematically depicts the housing distal end 46 in greater detail generally showing the formation of the patient's skin layers 50 (i.e., dermis 54 and epidermis 56) adjacent to the incision site 40, shortly after implantation of the housing 42. FIG. 3 schematically illustrates how, in a typical prior art implantation, the epidermis 56 and other tissue layers, over a period of time, can grow downwardly along the longitudinal surface 58 of the housing 42. This tissue downgrowth, as depicted in FIG. 3, tends to produce sinus tracts 59, susceptible for infection. Continued downgrowth can lead to marsupialization and ultimately can result in expulsion of the implant, e.g. hearing aid 30, from the patient's body.

The present invention is directed primarily to means for creating an infection resistant barrier around the housing distal end 46 at the percutaneous penetration, i.e., incision, site 40 in order to effectively anchor the implanted device and avoid the aforementioned problems associated with tissue downgrowth. Briefly, the infection resistant barrier is formed by promoting tissue ingrowth into a porous layer(s) formed on orthogonal (longitudinal and lateral) surfaces of the housing 42.

Figure 4:
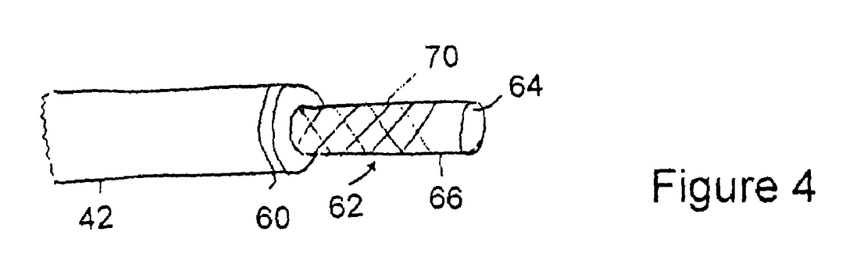
FIG. 4 schematically shows part of a device housing having a portion, or stud, adapted to project percutaneously in accordance with the invention having longitudinally and laterally extending surfaces for respectively supporting porous layers.
Figure 5:
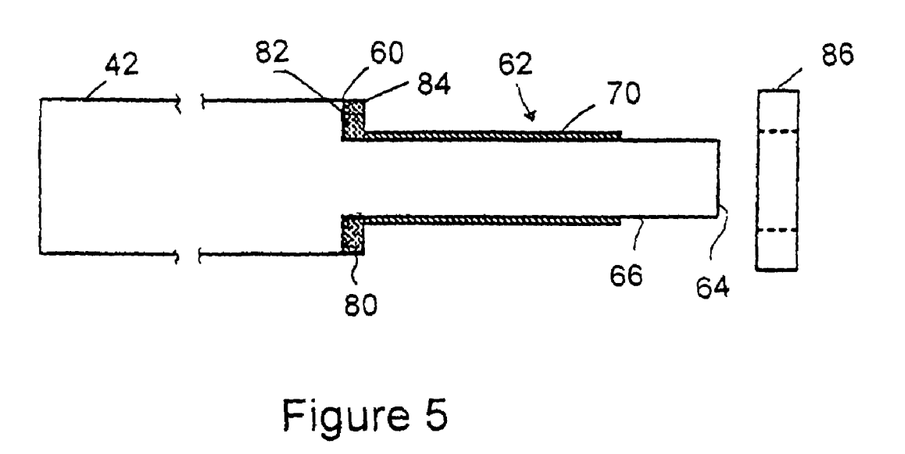
FIG. 5 is a side sectional view of the device housing of FIG. 4 also showing an optional end cap.

Attention is now directed to FIGS. 4 and 5 which illustrate a preferred manner of configuring the housing distal end 46 in accordance with the present invention. As shown, the housing 42 includes a lateral shoulder 60 which forms a reduced diameter stud 62 extending longitudinally therefrom and terminating at outer end surface 64. The stud 62 defines a longitudinally extending peripheral surface 66. The peripheral surface 66 typically has a circular cross section but other cross sectional shapes, e.g., oval, hexagonal, etc. can be used. Moreover, although, the outer end surface 64 is shown as being flat, in certain applications, it is preferable that the end surface have a different profile, e.g., conical or spherical.

Figure 6:
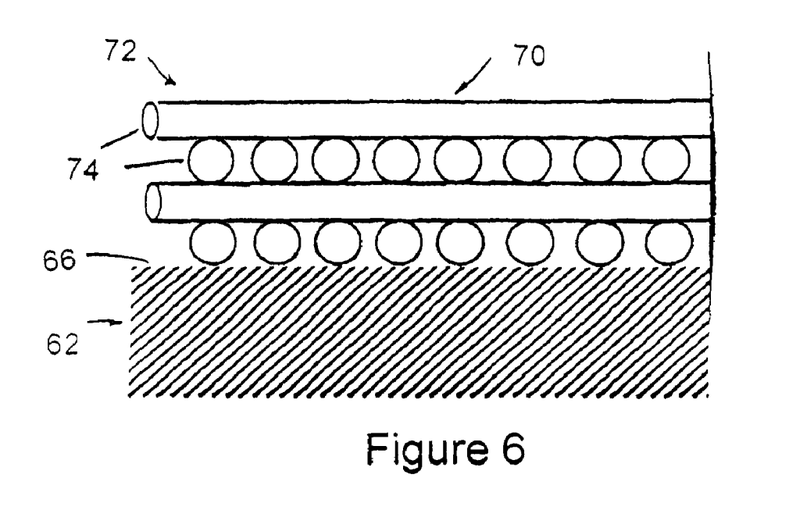
FIG. 6 is an enlarged schematic representation of a fibrous mesh which can form a porous layer in accordance with the invention.

In accordance with the invention, a first porous layer, or surface, 70 is formed along a longitudinally extending portion of the peripheral surface 66. The porous layer 70 is preferably formed by a mesh 72 of intersecting fibers 74 as depicted in FIG. 6. The fibers can be of any suitable biocompatible material such as a metal, e.g., titanium, nitinol, silver, or stainless steel or a polymeric material, e.g., polyolefins, Teflon, nylon, Dacron, or silicone. The mesh 72 is preferably formed by cross winding the fibers 74 in multiple layers to define a porosity conducive to promoting tissue ingrowth, e.g., with pore sizes within a range of 50 to 200 microns and having a porosity of 60 to 95%. The resulting porosity of the mesh 72 is a function of several factors including the diameter of the fibers 74 and the spacing between adjacent fibers.

The mesh 72 can be formed by directly winding the fibers 74 on the peripheral surface 66 acting as a substrate. Alternatively, the mesh 72 can be formed as an integral structure and then attached to the peripheral surface 66 by suitable mechanical or adhesive means. As an alternative to winding the fiber mesh 72, a porous surface 70 can be formed by a sintered mass of metal or polymeric material having the aforementioned porosity characteristics.

In accordance with the invention, as seen in FIG. 5, a second porous layer, or surface, 80 is provided oriented substantially perpendicular to the longitudinally extending porous surface 70. The porous layer 80 is formed on the laterally oriented surface 82 formed by shoulder 60. The porous layer 80 is preferably formed by a disk 84 formed of porous material having a central aperture for passing stud 62. The disk 84 can be adhered or mechanically attached to the lateral shoulder surface 82. The disk 84 can be formed of a fiber mesh (FIG. 6) or a sintered mass, as previously described, to provide porosity characteristics consistent with the previously mentioned porosity characteristics.

Figure 8:
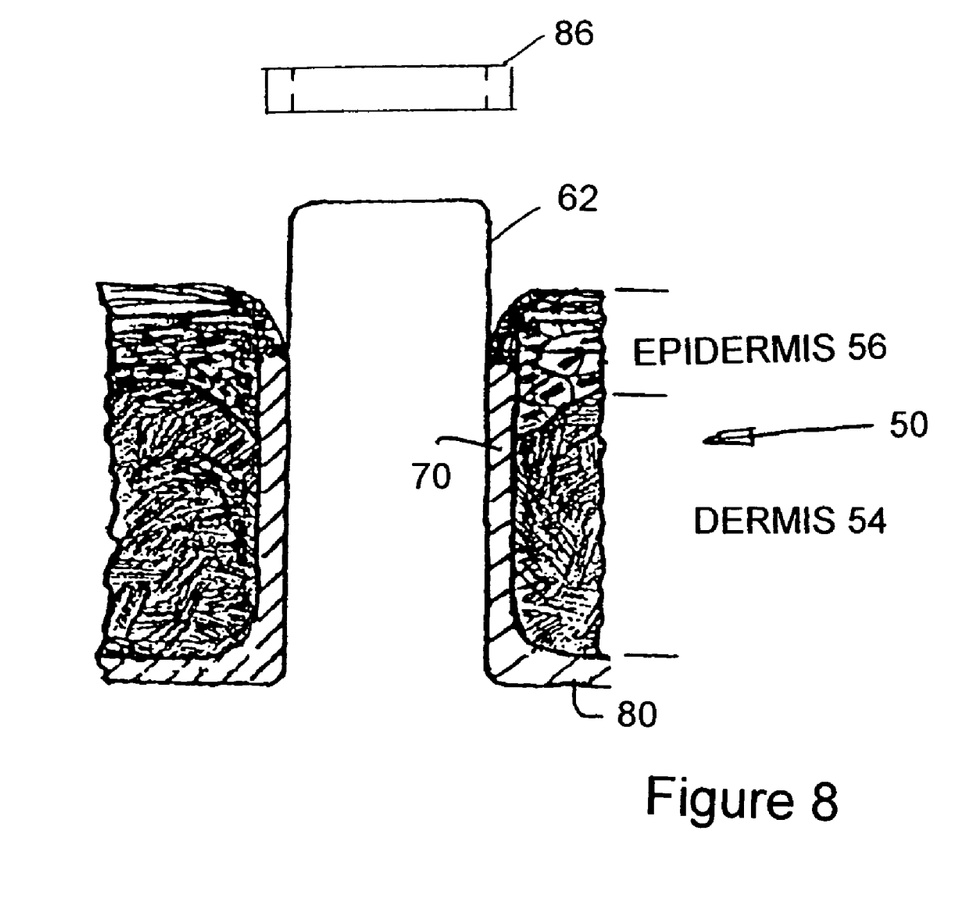
FIG. 8 is a schematic representation similar to FIG. 3 but representing tissue ingrowth into the interstices of longitudinal and lateral porous layers in accordance with the present invention.

FIG. 8 illustrates the stud 62 percutaneously penetrating the patient's skin layers 50 and shows how the soft tissue grows into the orthogonal porous layers 70 and 80 to create a closed infection resistant barrier around the stud. The ingrowth into the porous layers 70 and 80 additionally promotes vascularization as the dermis grows into and entwines with the mesh. It is also pointed out that FIG. 8 demonstrates the use of an optional cap 86 adapted to be mounted on the stud outer end for protection of the tissue around the incision during the healing process.

Figure 7:
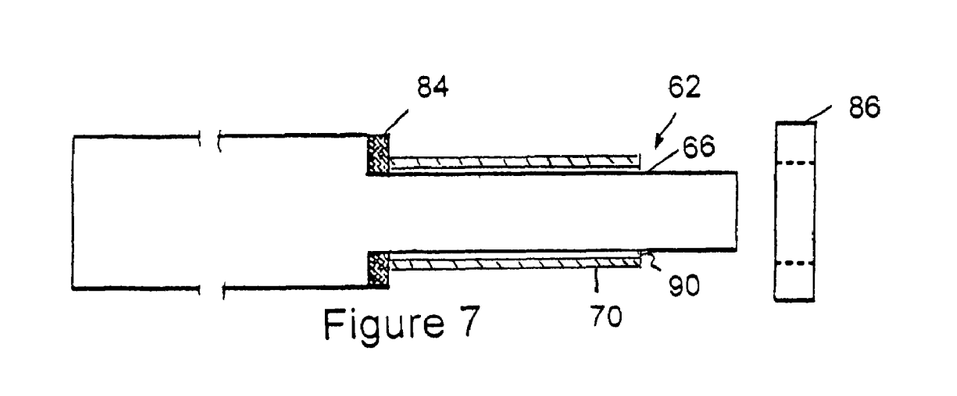
FIG. 7 is similar to FIG. 5 but additionally represents the inclusion of an optional supplemental agent for cooperating with the porous layer to promote tissue healing and/or resist infection and inflammation.

It is pointed out that it is sometimes desirable to include one or more substances on the stud 62 to promote tissue healing and/or resist infection and inflammation. Suitable substances are known in the literature and include, for example, antibiotics, silver compounds, and steroid based agents. Such substances can be deposited on the stud 62 as shown in FIG. 7, for example, as a sublayer 90 applied to the peripheral surface 66 beneath the porous layer 70. Alternatively, the substances can be incorporated within the mesh or sintered material of the porous layers 70 and 80.

Figure 9A:
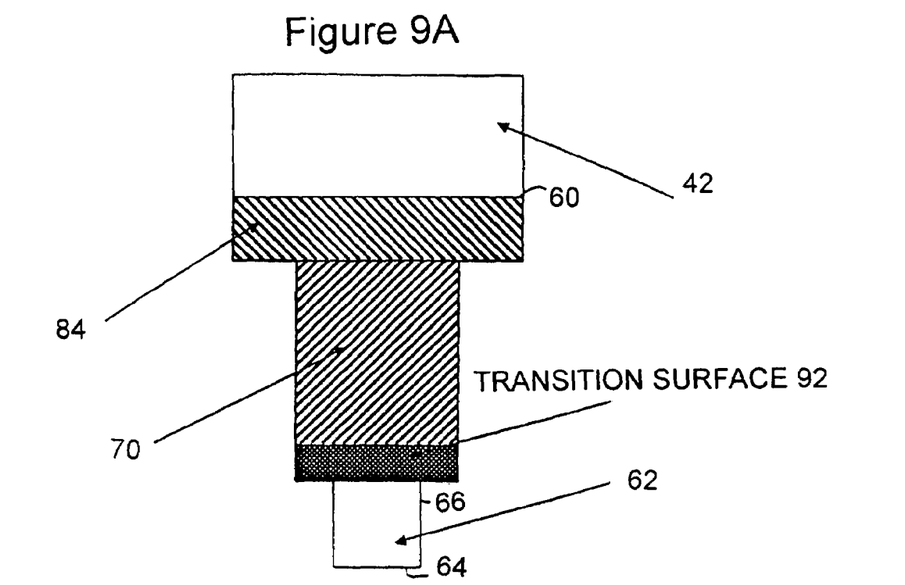
FIGS. 9A-9D illustrate various configurations showing the use of a transitional surface installed on a housing stud to beneficially modify healing.
Figure 9B:
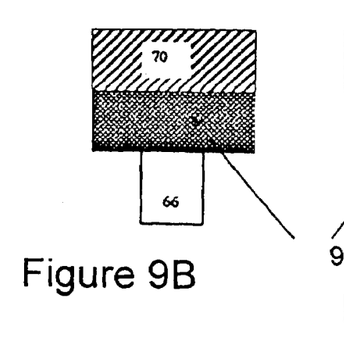
Figure 9C:
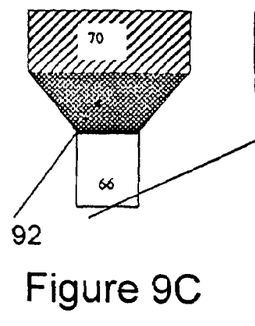
Figure 9D:
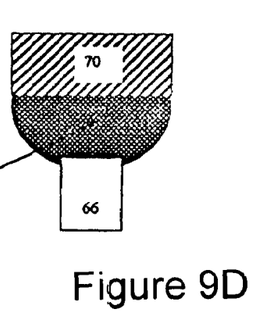

FIG. 9A depicts the device of FIGS. 4 and 5 but further shows the utilization of a transitional layer, or surface, 92 mounted on the stud peripheral surface 66 between the peripheral porous surface 70 and the stud outer end 64. The transitional surface 92 can have the same or a different porosity and/or composition as the porous surface 70 and can be variously configured as shown, for example, in FIGS. 9B, 9C, 9D. The transitional surface 92 is intended to beneficially modify the healing response of the adjacent tissue cells after implantation.

Figure 10:
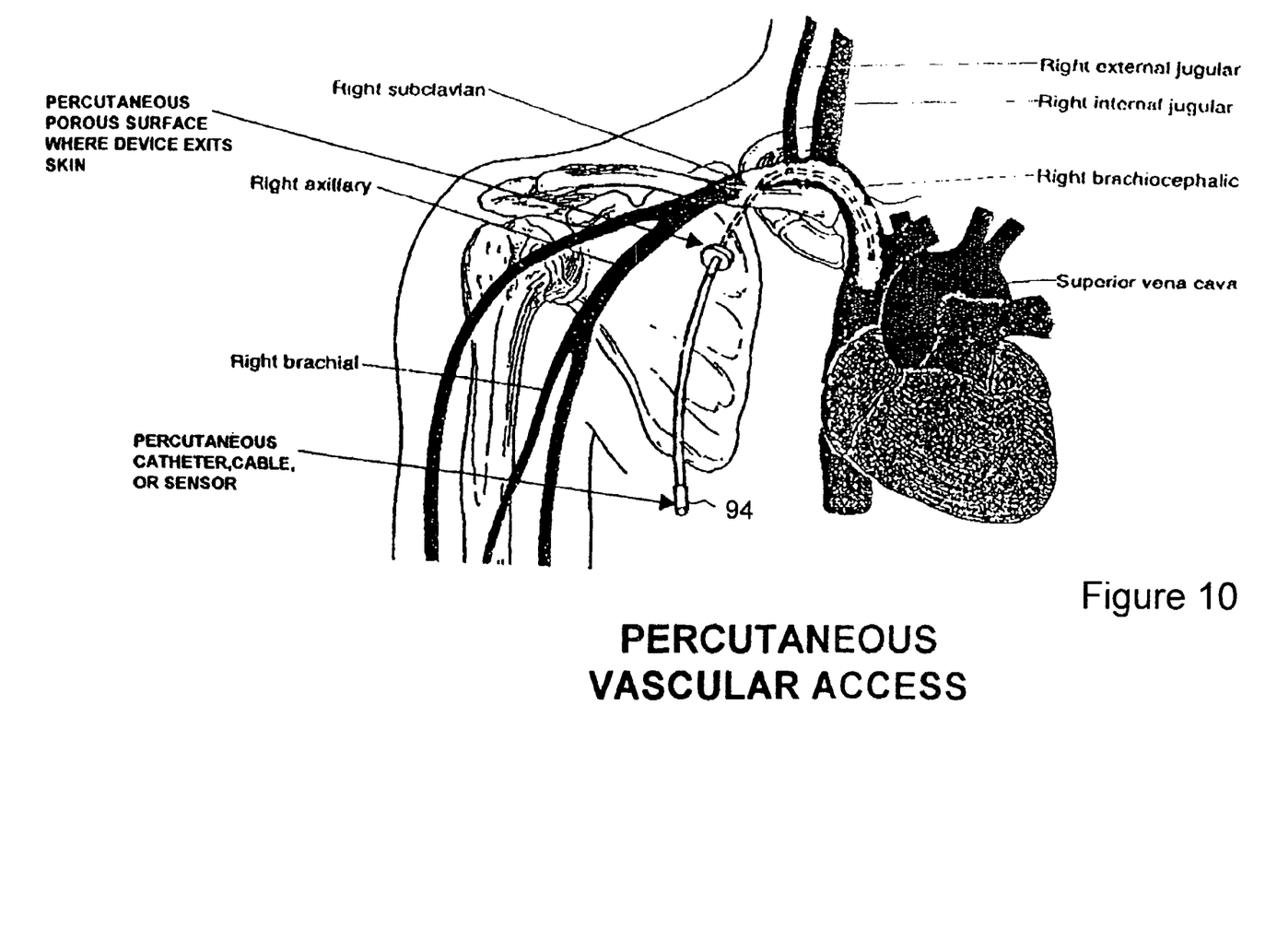
FIG. 10 schematically depicts the use of an invention embodiment in a vascular application where a catheter, cable, or sensor extends percutaneously through the patient's skin layers.
Figure 11:
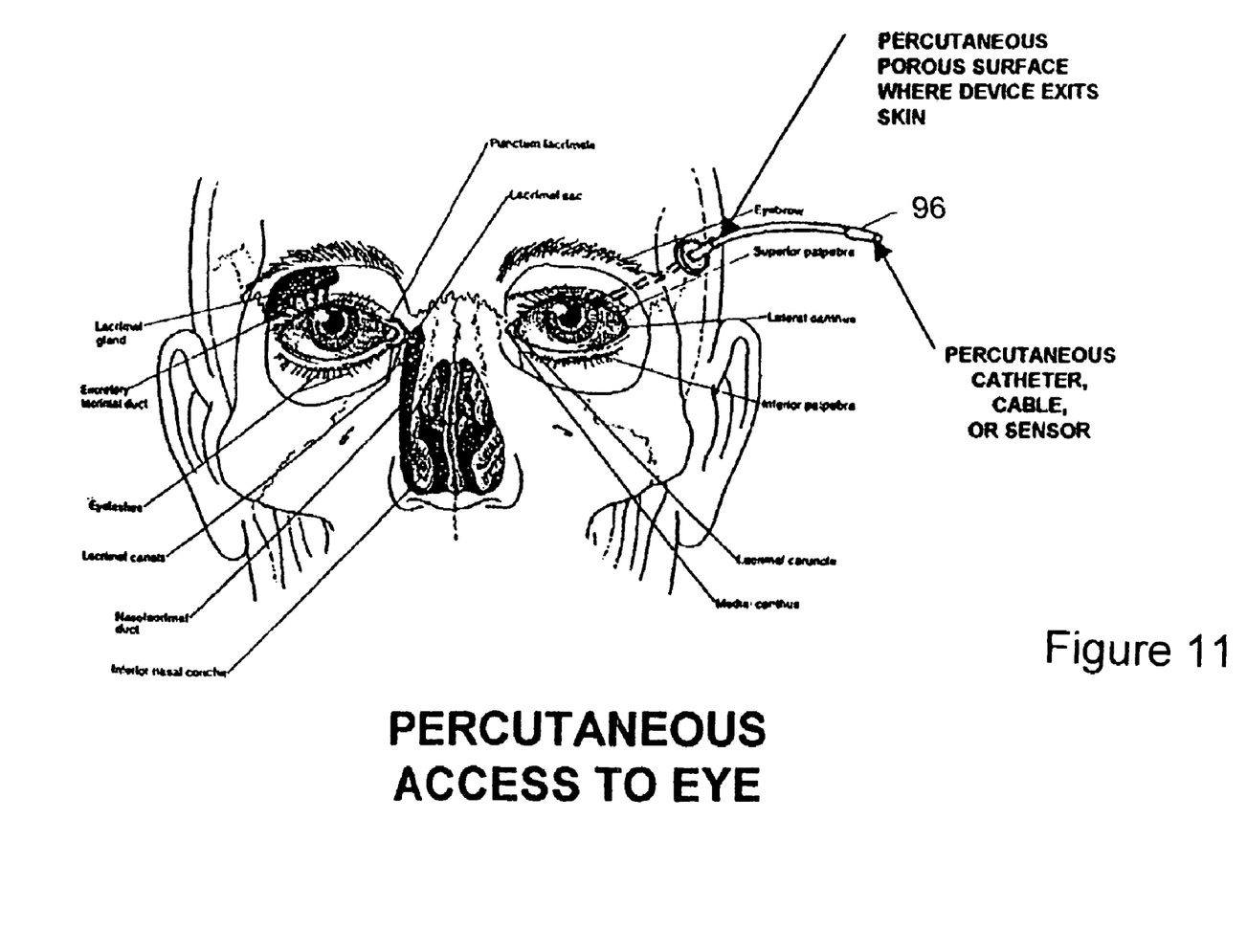
FIG. 11 schematically depicts the use of an invention embodiment in an ocular application for providing access to the inner eye via a percutaneous catheter, cable, or sensor.

For convenience in explanation, the description thus far has mostly merely referred to a "stud" percutaneously projecting through the patient's skin layers. It should be understood that the term "stud" as used herein, is not intended to connote any particular structural configuration but rather to generically refer to any member percutaneously projecting from an orthogonal shoulder surface. In different applications, the stud can variously comprise a catheter, a cable, a sensor or other member which projects percutaneously from a lateral shoulder surface. FIG. 10 depicts an exemplary application of the invention showing a catheter, cable, or sensor 94 which projects percutaneously for providing vascular access. FIG. 11 depicts a further exemplary application where a catheter, cable, or sensor 96 projects percutaneously for providing access to the inner eye.

Attention is now directed to FIGS. 12 and 13A, 13B, 13C which depict a preferred embodiment 100 of the invention configured for use as a hearing aid in the manner schematically represented in FIG. 1. The embodiment 100 comprises a housing 102 having a body portion 103 and a stud portion 104. The body 103 has a substantially rectangular (with rounded corners) cross-section (FIG. 13A) defined by short sides 105 and long sides 106. The body extends longitudinally in a forward direction from a rear face 108 to a laterally oriented shoulder surface 110. The stud 104 extends forwardly from the shoulder surface 110 and terminates at a stud outer face 114. The body 103 houses electronic circuitry (not shown) for driving a sound generator, e.g., electroacoustic transducer (not shown), mounted in the stud proximate to the outer face 114. It is intended that when implanted, the stud 104 will project percutaneously to place the stud face 114 in the patient's ear canal.

Figure 12:
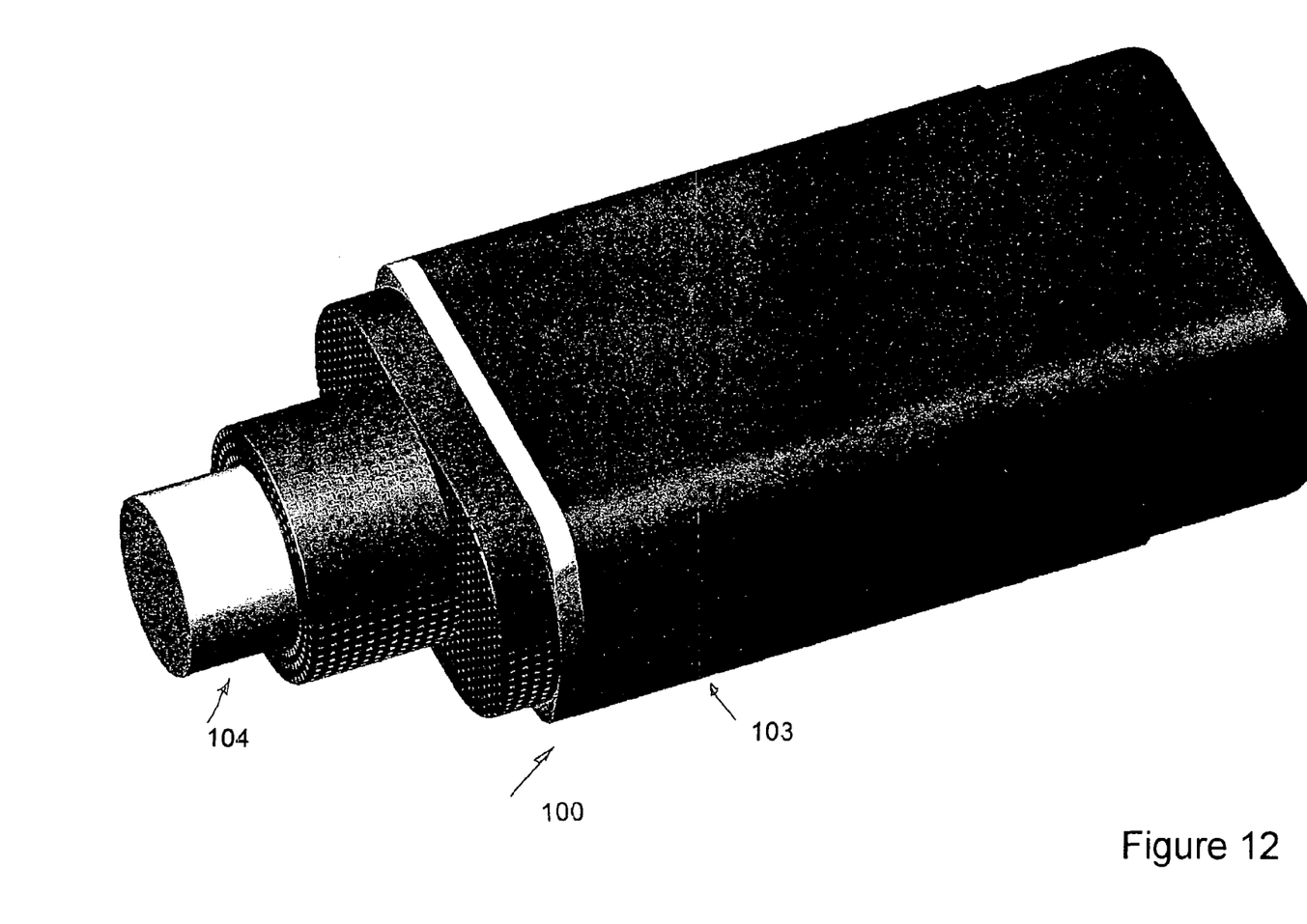
FIG. 12 is an isometric view of one preferred embodiment of the invention intended for implanting adjacent to a patient's ear canal to promote hearing (as generally depicted in FIG. 1)
Figure 13:
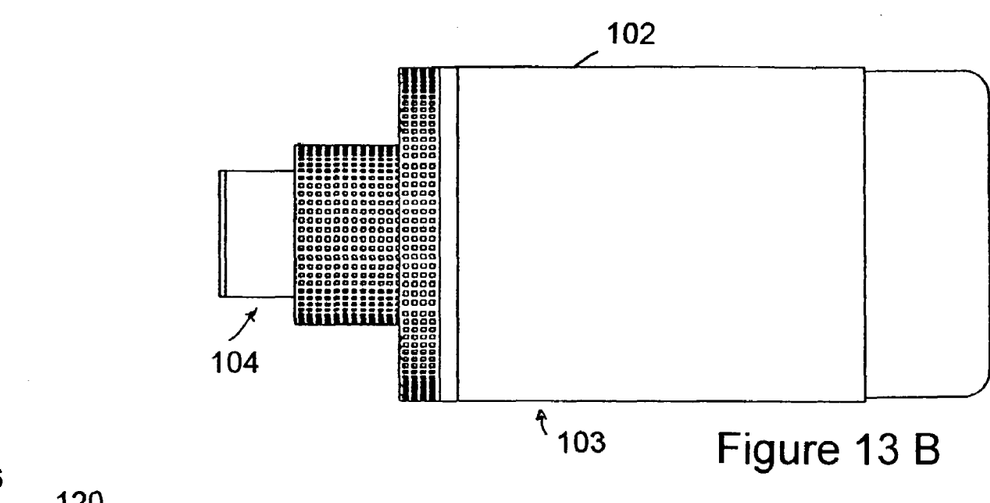
FIGS. 13A, 13B, and 13C respectively show top, side, and end views of the device of FIG. 12.

As previously described, in order to promote healthy tissue ingrowth for anchoring the housing 102 and forming a bacteria resistant barrier, a porous layer comprising a first portion of porous material 116 is formed on the longitudinally extending peripheral surface 118 of stud 104 and a second portion of porous material 120 is formed on the laterally extending shoulder surface 110.

From the foregoing, it should now be appreciated that the application describes a method and apparatus for creating an enhanced infection resistant barrier around a percutaneously projecting member. Embodiments of the invention are useful in a wide variety of medical applications for creating an infection resistant barrier, for effective anchoring, and for avoiding the development of adverse conditions such as marsupialization. Although only a limited number of embodiments have been specifically described herein, it should be recognized that modifications, variations and other equivalent arrangements will occur to those skilled in the art coming within the spirit of the invention and the intended scope of the appended claims.

The invention claimed is:

1. A medical device comprising:
    a housing body having a longitudinal peripheral surface defining a substantially uniform lateral dimension configured for subcutaneous implantation by surgical tunneling;
    a stud projecting longitudinally from said housing body configured for percutaneous implantation having an inner end adjacent to said housing body and an outer end spaced longitudinally therefrom to define a longitudinal peripheral surface;
    a shoulder surface on said housing body extending laterally from said housing body longitudinal peripheral surface to said stud longitudinal peripheral surface;
    a laterally extending first porous layer carried by said shoulder surface having a lateral dimension no greater than said housing body lateral dimension;
    a second porous layer carried by said stud longitudinal peripheral surface extending longitudinally from said first porous layer and terminating inwardly of said stud outer end, said second porous layer having a lateral dimension no greater than said housing body lateral dimension; and wherein
    said first and said second porous layers orthogonally abut one another and wherein each of said porous layers is characterized by a pore size within the range of 50 to 200 microns with a porosity of between 60 to 95% for promoting soft tissue ingrowth.

2. The medical device of claim 1 wherein at least one of said porous layers comprises a mesh of fibers.

3. The medical device of claim 2 wherein said fibers are of metal material from within a group comprised of titanium, nitinol, silver, and stainless steel.

4. The medical device of claim 2 wherein said fibers are of polymeric material.

5. The medical device of claim 1 wherein at least one of said porous layers comprises a mass of sintered material.

6. The medical device of claim 5 wherein said mass is formed of metal material from within a group comprised of titanium, nitinol, silver, and stainless steel.

7. The medical device of claim 5 wherein said mass is formed of polymeric material.

8. The medical device of claim 1 wherein said stud caries a sound generator and is configured to percutaneously project into a patient's ear canal.

9. The medical device of claim 1 wherein said stud comprises a portion of an implanted catheter providing access to an interior body site.

10. The medical device of claim 1 wherein said stud includes a sensor coupled to an interior body site.

11. A method of configuring a medical device for implantation by surgical tunneling from a proximal site to a distal site, said method comprising:
    providing a housing body having a longitudinal peripheral surface defining a substantially uniform lateral dimension suitable for subcutaneous implantation by surgical tunneling from said proximal site;
    providing a longitudinal stud projecting distally from said housing body, said stud having an inner end adjacent to said housing body and an outer end spaced longitudinally therefrom and defining a longitudinal peripheral surface;
    providing a shoulder surface extending laterally from said housing body peripheral surface to said stud longitudinal peripheral surface;
    forming a lateral porous layer on said shoulder surface having a lateral dimension no greater than said housing body lateral dimension and where said lateral porous layer is characterized by a pore size within the range of 50 to 200 microns with a porosity of between 60 to 95% for promoting soft tissue ingrowth;
    forming a longitudinal porous layer on said stud peripheral surface having a lateral dimension no greater than said housing body lateral dimension and where said longitudinal porous layer extends from said lateral porous layer to a location longitudinally inward of said stud outer end and is characterized by a pore size within the range of 50 to 200 microns with a porosity of between 60 to 95% for promoting soft tissue ingrowth; and positioning said longitudinal porous layer to orthogonally abut said lateral porous layer proximate to said shoulder surface.

12. The method of claim 11 wherein said step of forming a porous layer comprises forming at least a portion of said layer with a fiber mesh.

13. The method of claim 11 wherein said step of forming a porous layer comprises forming at least a portion of said layer with a mass of sintered material.

14. The method of claim 11 wherein each of said porous layers is formed at least in part of metal material from within a group comprised of titanium, nitinol, silver, and stainless steel.

15. The method of claim 11 wherein said porous layer is formed at least in part of polymeric material.

* * * * *